United States Patent [19]

Simon-Bierenbaum et al.

[11] 4,367,348

[45] Jan. 4, 1983

[54] NOVEL TRIFLUOROMETHYL BENZAL CHLORIDES AND PROCESS FOR THE PREPARATION THEREOF

[75] Inventors: R. Simon-Bierenbaum, Buffalo; David Y. Tang, Tonawanda, both of N.Y.

[73] Assignee: Occidental Chemical Corporation, Niagara Falls, N.Y.

[21] Appl. No.: 195,736

[22] Filed: Oct. 10, 1980

[51] Int. Cl.$^3$ .................. C07B 9/00; C07C 17/14; C07C 45/00
[52] U.S. Cl. .................................. 570/127; 568/437
[58] Field of Search .................. 570/127; 568/437

[56] References Cited

U.S. PATENT DOCUMENTS

| | | | |
|---|---|---|---|
| 2,180,772 | 11/1939 | Scherer | 568/437 |
| 3,465,051 | 9/1969 | Pecherer | 570/144 |
| 3,489,784 | 1/1970 | Feleg | 570/144 |
| 3,499,934 | 3/1970 | Pyne | 568/437 |
| 3,681,454 | 8/1972 | Rondestvedt | 260/544 M |
| 3,813,446 | 5/1974 | Jacobs | 570/127 |
| 4,079,089 | 3/1978 | Klauke | 570/127 |
| 4,079,090 | 3/1978 | Büttner | 570/127 |
| 4,093,669 | 6/1978 | Klauke et al. | 570/127 |
| 4,229,379 | 10/1980 | Brühne et al. | 568/437 |

OTHER PUBLICATIONS

Kobayashi et al., Accounts of Chem. Res. 11 (1978) pp. 197-204.
Hasek et al., J.A.C.S. 82 (1960) p. 543.
Mathey et al., Tetrahedron 31 (1975) pp. 391-401.
Belcher et al., Analytica Chimica Acta 10 (1954) pp. 34-47.
Fernandez-Bolaños et al., J. Chem. Soc. 1960, pp. 4003-4010.

*Primary Examiner*—Arthur P. Demers
*Attorney, Agent, or Firm*—J. F. Tao; A. S. Cookfair

[57] ABSTRACT

Novel meta- and para-trifluoromethyl benzal chlorides and ring-halogenated derivatives are useful chemical intermediates for the preparation of meta- and para-trifluoromethyl benzaldehydes and various other useful end products. The novel compounds can be prepared from readily-available xylene starting materials in a process comprising (a) chlorinating meta- or para-xylene, or a ring-halogenated meta- or para-xylene, to form a trichloromethyl benzal chloride product and (B) reacting the trichloromethyl benzal chloride product with about 3 moles or less of anhydrous hydrogen fluoride in the presence of a halogen exchange catalyst.

11 Claims, No Drawings

NOVEL TRIFLUOROMETHYL BENZAL CHLORIDES AND PROCESS FOR THE PREPARATION THEREOF

BACKGROUND OF THE INVENTION

This invention relates to novel compounds, in particular, meta- and para-trifluoromethyl benzal chlorides, and to a method for the preparation thereof. The meta- and para-trifluoromethyl benzal chlorides and ring-halogenated derivatives thereof useful as chemical intermediates for the production of pesticides and various other useful end products.

It is known from the chemical literature (Balanos et al, J. Chem. Soc., 4003, 1960; and Belcher et al, Anal. Chim. Acta, 10, 34, 1954) that o-trichloromethyl benzal chloride may be reacted with anhydrous hydrogen fluoride at elevated temperatures under high pressure, in the absence of a catalyst, to yield o-trifluoromethyl benzal chloride.

SUMMARY OF THE INVENTION

It has now been found that meta- or para-trifluoromethyl benzal chlorides of the formula

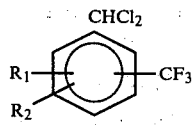

wherein $R_1$ and $R_2$ are independently selected from the group consisting of hydrogen, fluorine, chlorine and bromine are particularly advantageous chemical intermediates, for use in the preparation of m- or p-trifluoromethyl benzaldehyde, and various other useful end products. These novel and useful compounds may be prepared by contacting a meta- or para-trichloromethyl benzal chloride of the formula

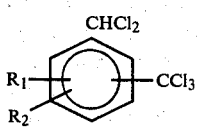

wherein $R_1$ and $R_2$ are as defined above, with anhydrous hydrogen fluoride in the presence of a halogen transfer catalyst.

It is a particular advantage of the process of this invention that meta- and para-trifluoromethyl benzal chlorides may be readily prepared in high yields at moderate temperatures and without the need for high pressures.

Various trichloromethyl benzal chlorides and substituted trichloromethyl benzal chlorides may be employed as reactants in the process of this invention to prepare correspondingly substituted or unsubstituted trifluoromethyl benzal chlorides. The preferred reactants for the process are the meta- and para-trichloromethyl benzal chlorides and the ring halogenated derivatives of these compounds, including, for example, 2-chloro-3-trichloromethyl benzal chloride; 2-chloro-5-trichloromethyl benzal chloride; 3-trichloromethyl-4-chloro benzal chloride; 3-chloro-5-trichloromethyl benzal chloride; 2,5-dichloro-3-trichloromethyl benzal chloride; 2,4-dichloro-3-trichloromethyl benzal chloride; 2,6-dichloro-3-trichloromethyl benzal chloride; 2-fluoro-3-trichloromethyl benzal chloride; 2-fluoro-5-trichloromethyl benzal chloride; 3-trichloromethyl-4-fluoro benzal chloride; 3-fluoro-5-trichloromethyl benzal chloride; 2,5-difluoro-3-trichloromethyl benzal chloride; 2-bromo-3-trichloromethyl benzal chloride; 2-bromo-5-trichloromethyl benzal chloride; 3-bromo-5-trichloromethyl benzal chloride; 2-chloro-4-trichloromethyl benzal chloride; 3-chloro-4-trichloromethyl benzal chloride; 2,5-dichloro-4-trichloromethyl benzal chloride; 2-fluoro-4-trichloromethyl benzal chloride; 3-fluoro-4-trichloromethyl benzal chloride; 2,5-difluoro-3-trichloromethyl benzal chloride; 2-bromo-4-trichloromethyl benzal chloride; 3-bromo-4-trichloromethyl benzal chloride and the like.

The fluorination is carried out in the presence of a halogen transfer catalyst. Such catalysts are well known in literature and include for example ferric chloride, aluminum chloride, molybdenum pentachloride, titanium tetrachloride, antimony pentafluoride, antimony pentachloride, antimony-V-chloride-fluoride, and the like. The preferred catalyst is antimony pentachloride. Typically, the catalyst is employed in amounts of about 0.1 to about 10 percent by weight and preferably about 0.5 to about 5 percent by weight based on the weight of trichloromethyl benzal chloride starting material. To assure completion of the reaction and maximum yield of the desired trifluoromethyl benzal chloride, it has been found advantageous to add more halogen transfer catalyst, such as about 0.1 to about 10 percent by weight based on the weight of the reaction mixture, after the addition of hydrogen fluoride is completed, and to maintain a temperature of about 40° to about 150° Celsius for an additional period of time, such as up to about two hours.

The fluorination may be carried out over a wide range of conditions. The process may be carried out at atmospheric pressure or at superatmospheric pressures, preferably in the range of up to about 3 atmospheres. The suitability of atmospheric pressure is a particular advantage and a preferred mode of the process of this invention. Process temperatures may vary considerably but are preferably in the range of about 40° to about 150° Celsius.

Although it is preferred to carry out the process neat, a suitable inert solvent, such as nitrobenzene, carbon disulfide and the like may be employed if desired.

The novel meta- and para-trifluoromethyl benzal chlorides of this invention may be economically prepared from readily available, inexpensive starting materials in a simple, direct manner, requiring relatively few process steps. Thus, for example, xylene may be chlorinated in a known manner such as photochlorination at temperatures in the range of about 20° to about 200° Celsius in the presence of actinic light, such as ultra violet light, while controlling the amount of chlorine reacted to yield a reaction product containing trichloromethyl benzal chloride as the major component. Over chlorinated components may be readily removed by physical separation means, such as distillation. Alternatively the crude reaction product may be employed in the fluorination step and unwanted components may be removed, if desired, following the fluorination step. The trichloromethyl benzal chloride is reacted with about three moles of anhydrous hydrogen fluoride in the presence of a halogen transfer catalyst in the manner described hereinabove to yield trifluoromethyl benzal chloride. Thus, in a simple direct method, meta- or para-trifluoromethyl benzal chloride may be synthesized from a readily available commodity chemical, such as meta- or para-xylene. In a similar manner, various ring-halogenated meta- or para-xylenes may be employed as starting materials to produce correspondingly substituted trifluoromethyl benzal chlorides.

In a particular embodiment, the present invention provides a process for the preparation of novel meta- or para-trifluoromethyl benzal chlorides comprising the steps of (A) chlorinating meta- or para-xylene, or a ring-halogenated meta- or para-xylene to form a trichloromethyl benzal chloride product, (B) reacting the trichloromethyl benzal chloride with about three moles or less of anhydrous hydrogen fluoride in the presence of a halogen transfer catalyst.

The meta- and para-trifluoromethyl benzal chloride, in accordance with this invention, are particularly useful as intermediates in the further preparation of meta- and para-trifluoromethyl benzaldehydes. Such preparation is readily accomplished by hydrolysis of the selected m- or p-trifluoromethyl benzal chloride. The hydrolysis reaction is carried out in the presence of about 0.1 to about 10 parts by weight of ferric chloride, based on the weight of benzal chloride, and is typically carried out at a temperature of about 75° to about 100° and preferably about 90° to about 100° Celsius. Thus, in another aspect the present invention provides a process for the preparation of meta- or para-trifluoromethyl benzaldehydes from meta- or para-xylenes comprising the steps of (A) chlorinating meta- or para-xylene or a ring-halogenated meta- or para-xylene, to form a trichloromethyl benzal chloride product, (B) reacting the trichloromethyl benzal chloride with about 3 moles or less of anhydrous hydrogen fluoride in the presence of a halogen transfer catalyst to form the corresponding trifluoromethyl benzal chloride, and (C) hydrolysis of the latter to form the corresponding meta- or para-trifluoromethyl benzaldehyde.

The following specific examples are provided to further illustrate the invention in a manner in which they be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1

A mixture of 99.5 parts of p-trichloromethyl benzal chloride and about 1.5 parts of antimony pentachloride was heated and maintained at a temperature of 75°–77° C. with stirring while 22 parts of hydrogen fluoride was added slowly over a period about 11 minutes. The reaction mixture was maintained at about that temperature, with stirring, for an additional hour, then purged with nitrogen and cooled to room temperature. The reaction product was treated with methylene chloride and with sodium carbonate, filtered to remove the sodium carbonate and catalyst, then distilled to remove methylene chloride. The remaining reaction product, 620 parts, was analyzed by gas chromatographic techniques and found to contain about 85.6% of p-trifluoromethyl benzal chloride, representing a yield of about 65% based on the p-trichloromethyl benzal chloride reactant.

EXAMPLE 2

The procedure of Example 1 is repeated except that in place of the p-trichloromethyl benzal chloride reactant, there is substituted an approximately equimolar amount of 2-chloro-4-trichloromethyl benzal chloride. The fluorination reaction product contains as a major component thereof, 2-chloro-4-trifluoromethyl benzal chloride.

EXAMPLE 3

Following the general procedure of Example 1, a mixture of 100 parts of p-trichloromethyl benzal chloride and about 1.5 parts of antimony pentachloride was heated and maintained at about 89°–99° C. while 26 parts of hydrogen fluoride was added slowly with stirring over a period of about 13 minutes. The temperature was maintained, and stirring continued for an additional 1.5 hours. The reaction mixture was then cooled to room temperature, purged with nitrogen; treated with methylene chloride and with sodium carbonate; filtered; and the methylene chloride removed by distillation. The remaining crude reaction product (36 parts by weight) was analyzed by gas chromatography and found to contain approximately 76% of p-trifluoromethyl benzal chloride.

EXAMPLE 4

P-xylene was heated to 150° C. and irradiated with an ultraviolet light source while chlorine gas was bubbled in. The photochlorination was continued until pentachloroxylene (i.e. p-trichloromethyl benzal chloride) constituted greater than 50% of the reaction mixture. The reaction mixture was then distilled using a packed column at a pressure of 5 torr and a pot temperature of 180° C. A major fraction comprising about 70.8% of p-trichloromethyl benzal chloride, taken at a head temperature of about 145° to 149° C. was separated from the reaction mixture. A mixture of 127 parts of this major fraction and 1.33 parts of antimony pentachloride was heated to 110° C. and maintained at that temperature while 34 parts of anhydrous hydrogen fluoride was added over a 3 hour period. The mixture was cooled to about 50° C. The excess hydrogen fluoride was removed and an additional 1.33 parts of antimony pentachloride added. After two hours the reaction mixture was cooled to about 25° C., slurried with sodium carbonate, filtered, washed with 6 N hydrochloric acid, and dried. Distillation at 5 torr, 98° C., yielded 32 parts of p-trifluoromethyl benzal chloride.

EXAMPLE 5

Following the procedure of Example 4, m-xylene is heated to about 150° C. and irradiated with ultraviolet light while chlorine gas is bubbled in until pentachloroxylene (i.e. m-trichloromethyl benzal chloride constitutes greater than 50% of the reaction mixture. The reaction mixture is distilled to separate a fraction thereof having a higher concentration of the m-trichloromethyl benzal chloride. This fraction is then mixed with 1 to 2 parts of antimony pentachloride and the mixture heated to about 110° C. and maintained thereat while about 34 parts of hydrogen fluoride is added over about a 3 hour period. The reaction product includes m-trifluoromethyl benzal chloride as a major component thereof.

EXAMPLE 6

The procedure of Example 1 is repeated except that in place of the p-trichloromethyl benzal chloride reactant there is substituted an approximately equimolar amount of 2,5-dichloro-3-trichloromethyl benzal chloride, and the temperature of the reaction is increased to about 115° C. Following the fluorination reaction the product 2,5-dichloro-3-trifluoromethyl benzal chloride is recovered from the reaction mixture.

EXAMPLE 7

A mixture of 128 parts of p-trifluoromethyl benzal chloride and 0.5 parts of ferric chloride was heated to about 95°–100° C., and maintained at that temperature, with stirring, while 10 parts of water was added slowly, over a period of 3 hours. The reaction mixture was retained at temperature, with stirring, for an additional hour, then distilled to separate 80 parts of p-trifluoromethyl benzaldehyde (b.p. 72° at 15 torr), having a purity of 97%, based on analysis by gas chromatographic techniques. The yield of p-trifluoromethyl benzaldehyde was about 85%, based on p-trifluoromethyl benzal chloride reactant.

What is claimed is:

1. m-trifluoromethyl benzal chloride.
2. p-trifluoromethyl benzal chloride.
3. A process for the preparation of meta- or para-trifluoromethyl benzal chlorides of the formula

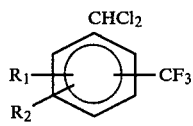

wherein $R_1$ and $R_2$ are independently selected from the group consisting of hydrogen, fluorine, chlorine and bromine, which comprises (A) chlorinating meta- or para-xylene of the formula

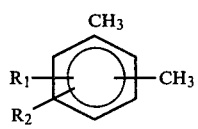

where $R_1$ and $R_2$ are as previously defined to form trichloromethyl benzal chloride of the formula

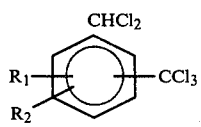

where $R_1$ and $R_2$ are as previously defined; and
(B) reacting the trichloromethyl benzal chloride with about 3 moles or less of anhydrous hydrogen fluoride in the presence of a halogen transfer catalyst.

4. A process according to claim 3 wherein the xylene of step (A) is m-xylene, and the product of step (B) is m-trifluoromethyl benzal chloride.
5. A process according to claim 3 wherein the xylene of step (A) is p-xylene and the product of step (B) is p-trifluoromethyl benzal chloride.
6. A process according to claim 5 wherein step (B) is carried out at a temperature of about 40° to about 150° Celsius.
7. A process according to claim 6 wherein the halogen transfer catalyst is antimony pentachloride.
8. A process for the preparation of m- or p-trifluoromethyl benzaldehyde of the formula

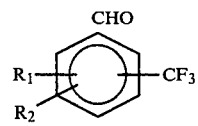

wherein $R_1$ and $R_2$ are independently selected from the group consisting of hydrogen fluorine, chlorine, and bromine, which comprises (A) chlorinating meta- or para-xylene of the formula

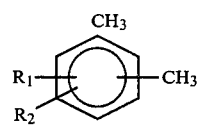

where $R_1$ and $R_2$ are as previously defined to form trichloromethyl benzal chloride of the formula

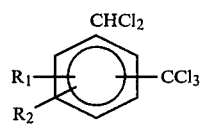

where $R_1$ and $R_2$ are as previously defined; and
(B) reacting the trichloromethyl benzal chloride with about 3 moles or less of anhydrous hydrogen fluoride in the presence of a halogen transfer catalyst to form a trifluoromethyl benzal chloride of the formula

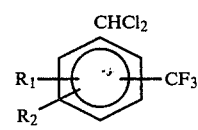

where $R_1$ and $R_2$ are as previously defined; and
(C) hydrolyzing the trifluoromethyl benzal chloride to form a trifluoromethyl benzaldehyde product.

9. A process according to claim 8 wherein the xylene of step A is m-xylene and the product of step (C) is m-trifluoromethyl benzaldehyde.
10. A process according to claim 8 wherein the xylene of step (A) is p-xylene and the product of step (C) is p-trifluoromethyl benzaldehyde.
11. A process according to claim 10 wherein the halogen transfer catalyst is antimony pentachloride.

* * * * *